US00PP12575P2

(12) United States Plant Patent

Olesen et al.

(10) Patent No.: US PP12,575 P2

(45) Date of Patent: Apr. 23, 2002

(54) SHRUB ROSE PLANT NAMED 'POULBUT'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/261,448

(22) Filed: Mar. 3, 1999

(51) Int. Cl.[7] ..... A01H 5/00

(52) U.S. Cl. ..... Plt./107

(58) Field of Search ..... Plt./101, 107, 121

(56) References Cited

PUBLICATIONS

Copy of Proposal for a Variety Denomination dated Jan. 27, 1997, and Copy of EU 3218 granted Jul 20, 1998 and Application EU–97/0136, filed Jan. 27, 1997.*

Copy of PL 01155, granted Feb. 24, 2000.*

UPOV–ROM, 2000/06, Plant Variety Database, GTI Jouve Retrieval Software, citation for 'POULbut'.*

UPOV–ROM, 2000/04, Plant Variety Database, GTI Jouve Retrieval Software, citation for 'POULbut'.*

* cited by examiner

*Primary Examiner*—Howard J. Locker

(57) ABSTRACT

A new shrub rose plant which has abundant, non-fading, light pink flowers and attractive foliage. This new and distinct variety has shown to be uniform and stable in the resulting generations from asexual propagation.

1 Drawing Sheet

SUMMARY OF THE INVENTION

The present invention constitutes a new and distinct variety of ground cover rose plant which originated from a controlled crossing conducted in spring 1990 between Bonica 82 and an unnamed seedling. The two parents were crossed and the resulting seeds were planted in a controlled environment. The new variety is named 'POULbut'.

The new rose may be distinguished from its seed parent, Bonica 82, by the following combination of characteristics:

1. The seed parent has soft pink flowers which are 60 mm in diameter with 35 to 40 petals while 'POULbut' has light pink single flowers with 6–8 petals which are 35–40 mm in diameter.

2. The seed parent is bushy and somewhat compact, while 'POULbut' is a low growing ground cover rose with spreading canes.

The new variety may be distinguished from its pollen parent, an unnamed unpatented seedling created by the same inventors, by the following combination of characteristics:

1. The pollen parent has white, small, semi-double flowers in clusters, while 'POULbut' has light pink single flowers with 6–8 petals which are 35–40 mm in diameter.

2. One of the parents of the unnamed seedling is 'POULcat', a groundcover rose by the same inventors.

The objective of the hybridization of this rose variety for commercial greenhouse culture was to create a new and distinct variety with unique qualities, such as:

1. Abundant, light pink flowers;

2. A low growing ground cover rose with uniform growth and a spreading habit;

3. Glossy and disease resistant foliage which requires limited maintenance, making it ideal for use in landscapes; and 4. Good growth on its own roots as well as a traditionally budded plant.

This combination of qualities is not present in previously available commerical cultivars of this type and distinguish 'POULbut' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULbut' was selected by the inventors in the spring of 1991 as a single plant from the progeny of the aforementioned hybridization. Asexual reproduction of 'POULbut' by traditional budding was first done by L. Pernille and Mogens N. Olesen in their nursery in Fredensborg, Denmark in August, 1991. This initial and other subsequent propagations conducted in controlled environments have demonstrated that the characteristics of 'POULbut' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULbut'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULbut', as observed in its growth during September, 1998 in a field nursery in Jackson County, Oreg. Color references are made using The Royal Horticultural Society (London, England) Colour Chart, 1995, except where common terms of color are used.

For a comparison, several physical characteristics of the rose variety 'POULlen', a shrub rose variety from the same inventors described and illustrated in U.S. Plant Pat. No. 9,273 and issued on Sep. 5, 1995 are compared to 'POULbut' in Chart 1.

CHART 1

| | 'POULbut' | 'POULlen' |
|---|---|---|
| Petal, color, upper surface open flower | Red Group 56D. | Red Group 56B. |
| Petal color, reverse surface open flower | Red Group 56D. | Red Group 55C. |
| Petal count per flower. | Single. 6–8 petals under normal conditions | Double. 33 to 37 petals under normal conditions. |

Parents:
- *Seed parent.*—Bonica 82.
- *Pollen parent.*—Unnamed, unpatented seedling.

Classification:
- *Botanical.*—*Rosa hybrida.*
- *Commercial.*—Ground cover.

FLOWER AND FLOWER BUD

Blooming habit: Recurrent.

Flower bud:
- *Size.*—Upon opening, 15 mm in length from base of receptacle to end of bud.
- *Bud form.*—Pointed ovoid.
- *Bud color.*—As sepals unfold, Red Group 52D. Red Group 49B at ¼ opening.
- *Sepals.*—Yellow-Green Group 144A. Weak foliaceous appendages on three of the five sepals. Surfaces of sepals slightly pubescent. Limited numbers of stipitate glands are present on margins and outer surfaces of sepals with extensions.
- *Receptacle.*—Surface: With moderate numbers of white hairs. Shape: Pear-shaped. Size: Small. 4 mm (h)×3 mm (w). Color: Green Group 144A.
- *Peduncle.*—Surface: With numerous stipitate glands and white hairs. Length: 18–22 mm average length. Color: Yellow-Green Group 144B. Strength: Erect.
- *Borne.*—Multiple buds per stem. Generally with 15–25 buds per flowering stem.

Flower bloom:
- *Fragrance.*—None.
- *Duration.*—The blooms have a duration on the plant of approximately 2 to 3 days. Petals fall cleanly away from plant.
- *Size.*—Small. Average flower diameter is 35–40 mm when open.
- *Form.*—Shape of flower when viewed from the side: Upon opening, upper part: Convex. Upon opening, lower part: Convex. Open flower, upper part: Flattened convex. Open flower, lower part: Flat.
- *Petalage.*—Single. Average range: 6–8 petals under normal conditions with 0–2 petaloids.

Color:
- *Upon opening, petals.*—Petals: Upper Surface: Red Group 49C. Reverse Side: Red Group 49B.
- *Upon opening, basal petal spots.*—Outer Side: Green-White Group 157C. Inner Side: Green-White Group 157C.
- *After opening, petals.*—Petals: Upper Surface: Red Group 56D. Reverse Side: Red Group 56D.
- *After opening, basal petal spots.*—Outer Side: Green-White Group 157D. Inner Side: Green-White Group 157D.

General tonality: On open flower Red Group 56D. No change in the general tonality at the end of the second day. Afterwards, general tonality is Red Group 36D.

Petals:
- *Petal reflex.*—None.
- *Petal edge.*—Uniform. With point in center of margin.
- *Shape.*—Deltoid.
- *Petaloids.*—Few.
- *Thickness.*—Thin.
- *Arrangement.*—Informal.

Reproductive organs:
- *Pollen.*—Color: Yellow-Orange Group 17C. Abundance: Average.
- *Anthers.*—Size: Medium. Color, immature: Greyed-Orange Group 168C to Yellow Group 13D. Color, mature: Greyed-Orange Group 165D. Abundance: Average.
- *Filaments.*—Color: Green-Yellow Group 1B.
- *Stigmas.*—Limited numbers of female floral parts. Stigmas located at same position as anthers. Color: Yellow-Green Group 145D.
- *Styles.*—With limited hairs on styles. Color: Yellow-Green Group 145C. Other intonations: Below stigma, style is Greyed-Purple 185B.
- *Ovary.*—Half inferior.
- *Hip formation.*—None observed.

PLANT

Plant growth: Ground cover with spreading habit. When grown as a budded field grown plant on *R. multiflora* understock, the average height of the plant itself is 20–25 cm and the average width is 90–100 cm.

Stems:
- *Color.*—Young wood: Yellow-Green Group 144B. Older wood: Yellow-Green Group 146B.
- *Prickles.*—Incidence: Moderate. Size: Smaller prickles from 4 to 5 mm long; larger prickles from 5 to 9 mm long. Color: Young: Red Group 39B–C. Mature: Greyed-Orange Group 167D. Shape: Linear.
- *Surface.*—Young wood: Smooth. Older wood: Smooth.

Plant foliage: Normal number of leaflets on normal leaves in middle of the stem: 5–7 leaflets. On leaves with 7 leaflets, lower leaflets are reduced in size.
- *Leaf size: Small.* 60 mm (l)×30–35 mm (w).
- *Abundance.*—Average to above average abundance.
- *Color.*—Upper Leaf Surface: Green Group 137A. Lower Leaf Surface: Green Group 138B. Juvenile foliage: Upper side: Green Group 137A. Lower side: Green Group 137A. Anthocyanin intonation: Limited. Location: Thorns, peduncles, leaflet rachis, and leaf petioles. Color: Greyed-Red Group 179A.

Plant leaves and leaflets:
- *Stipules.*—Size: 10 mm–12 mm. Color: Green Group 143B. Presence of stipitate glands: Stipitate glands present on margins of most stipules.

*Petiole.*—Length: 14 mm–18 mm. Color: Green Group 137A. Underneath: Some with prickles and a few stipitate glands. Mostly smooth, glabrous. Margins: With stipitate glands and limited numbers of fine white hairs.

*Rachis.*—Color: Green Group 137A. Underneath: Some with prickles and a few stipitate glands. Mostly smooth, glabrous. Margins: With stipitate glands and limited numbers of fine white hairs.

*Leaflet.*—Edge: Serrated. Shape: Ovate. Other: Moderately glossy finish. Thin texture.

Disease resistance: Above average resistance to mildew and Black spot under normal growing conditions in Jackson County, Oreg.

Winter hardiness: Winter hardy in Denmark and in Jackson County, Oreg.

We claim:

1. A new and distinct variety of rose plant of the ground cover class, substantially as herein illlustrated and described as a distinct and novel rose variety due to its abundant, light pink flowers, spreading habit, and disease resistance.

* * * * *

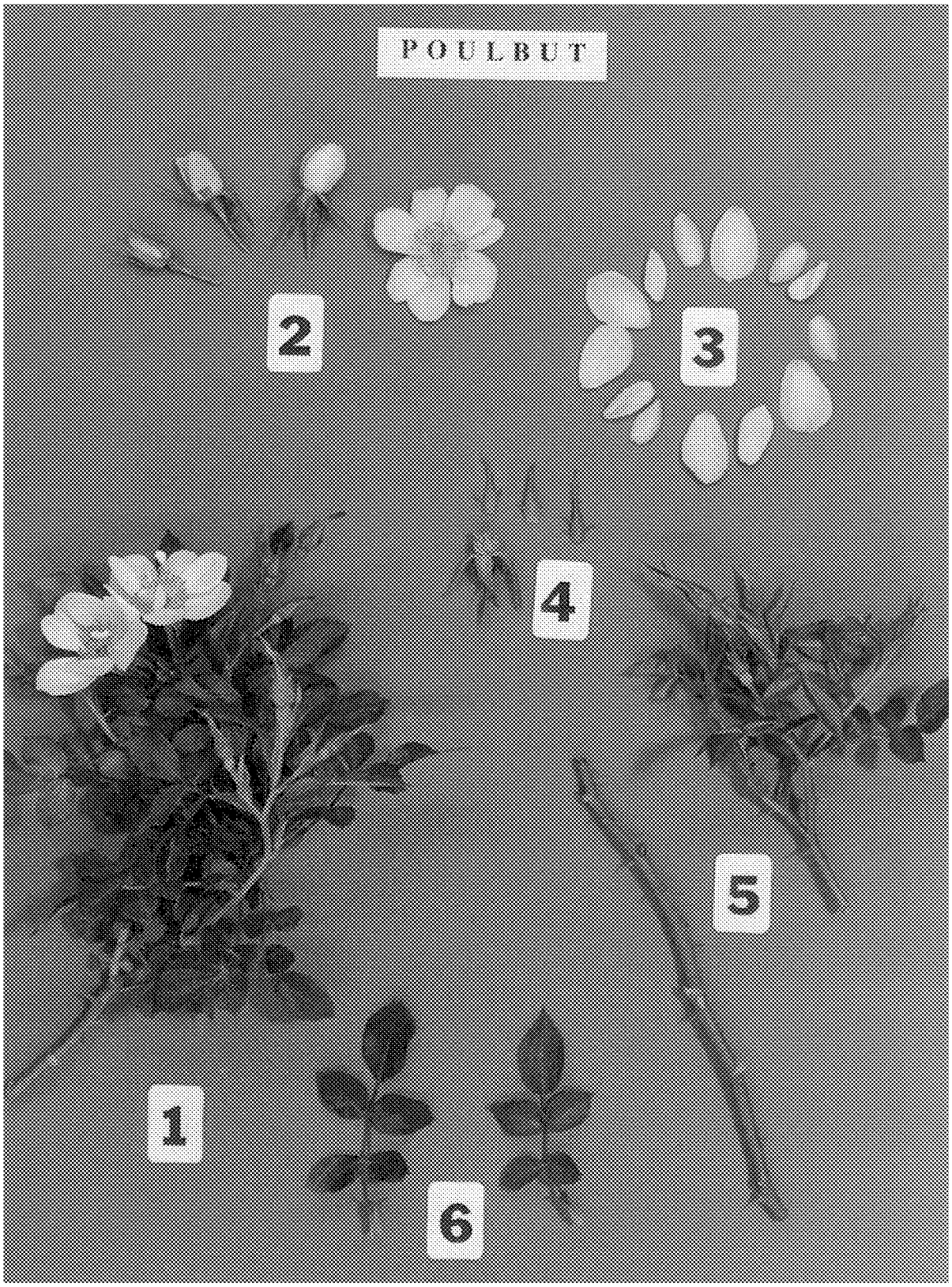
POULBUT
2
3
4
5
1
6